(12) United States Patent
Benson et al.

(10) Patent No.: US 10,172,719 B2
(45) Date of Patent: Jan. 8, 2019

(54) SURGICAL SYSTEM AND METHOD OF USE

(71) Applicant: Warsaw Orthopedic, Inc, Warsaw, IN (US)

(72) Inventors: Nicholas M. Benson, Cordova, TN (US); Rodney Ray Ballard, Lakeland, TN (US); James M. Mirda, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/432,648

(22) Filed: Feb. 14, 2017

(65) Prior Publication Data

US 2018/0228623 A1 Aug. 16, 2018

(51) Int. Cl.
*A61B 17/88* (2006.01)
*A61F 2/44* (2006.01)
*A61B 17/70* (2006.01)
*A61B 34/20* (2016.01)

(52) U.S. Cl.
CPC ........ *A61F 2/4455* (2013.01); *A61B 17/7001* (2013.01); *A61B 17/7067* (2013.01); *A61B 17/7068* (2013.01); *A61B 34/20* (2016.02); *A61F 2/442* (2013.01); *A61B 2034/2055* (2016.02); *A61B 2034/2065* (2016.02)

(58) Field of Classification Search
CPC ........ A61F 2/4455; A61F 2/442; A61B 34/20; A61B 17/7001; A61B 17/7067; A61B 17/7068; A61B 2034/2055; A61B 2034/2065

USPC ............... 606/279, 246, 102, 105; 623/17.16
See application file for complete search history.

(56) References Cited

U.S. PATENT DOCUMENTS

| | | | |
|---|---|---|---|
| 5,207,678 A | 5/1993 | Harms et al. | |
| 5,575,792 A | 11/1996 | Errico et al. | |
| 5,609,593 A | 3/1997 | Errico et al. | |
| 5,609,654 A | 3/1997 | Le et al. | |
| 5,630,817 A | 5/1997 | Rokegem et al. | |
| 5,643,263 A | 7/1997 | Simonson | |
| 5,797,911 A | 8/1998 | Sherman et al. | |
| 5,885,285 A | 3/1999 | Simonson | |
| 5,947,967 A | 9/1999 | Barker | |
| 6,074,391 A | 6/2000 | Metz-Stavenhagen et al. | |
| 6,280,442 B1 | 8/2001 | Barker et al. | |
| 6,520,962 B1 | 2/2003 | Taylor et al. | |
| 6,562,038 B1 | 5/2003 | Morrison | |
| 6,572,618 B1 | 6/2003 | Morrison | |
| 6,579,292 B2 | 6/2003 | Taylor | |
| 6,648,887 B2 | 11/2003 | Ashman | |
| 6,685,705 B1 | 2/2004 | Taylor | |
| 6,755,830 B2 | 6/2004 | Mindelde et al. | |
| 6,872,209 B2 | 3/2005 | Morrison | |
| 7,066,939 B2 | 6/2006 | Taylor | |
| 8,585,741 B2 | 11/2013 | Gabelberger et al. | |

(Continued)

*Primary Examiner* — Pedro Philogene
*Assistant Examiner* — David C Comstock

(57) ABSTRACT

A method for treating a spine is provided. The method includes the steps of: pre-operatively measuring a first portion of intervertebral tissue adjacent to a neural foramen; intra-operatively measuring a second portion of the intervertebral tissue adjacent to the neural foramen; generating a threshold value based on the measured portions; and selecting an interbody implant based on the threshold value. Spinal implants, surgical instruments and systems are disclosed.

19 Claims, 11 Drawing Sheets

(56) References Cited

U.S. PATENT DOCUMENTS

| | | |
|---|---|---|
| 9,314,274 B2 | 4/2016 | Amstutz et al. |
| 9,402,663 B2 | 8/2016 | Peterson et al. |
| 2006/0074431 A1 | 4/2006 | Sutton et al. |
| 2010/0331883 A1* | 12/2010 | Schmitz ............ A61B 10/0275 606/249 |
| 2015/0282797 A1 | 10/2015 | O'Neil et al. |

* cited by examiner

SURGICAL SYSTEM AND METHOD OF USE

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative, isthmic and iatrogenic spondylolisthesis, degenerative disc disease, disc herniation, and stenosis may result from disease and degenerative conditions caused by injury, prior surgery and aging. These spinal disorders typically result in symptoms including deformity, pain, nerve damage, and partial or complete loss of mobility. Kyphosis and lysthesis or anterior translation of one vertebra in relation to the next may occur in many of these conditions and pathologies.

Non-surgical treatments, such as medication, rehabilitation and exercise can be effective, however, may fail to relieve the symptoms associated with these disorders. Current surgical treatment of these spinal disorders includes decompression and restoration of the normal alignment of the spine with concomitant fusion. Techniques used to commonly achieve these goals may include laminectomy, discectomy, fusion, internal spinal fixation, correction of the kyphotic deformity and the insertion of implantable interbody prosthetics. As part of these surgical treatments, spinal constructs, such as, for example, bone fasteners, spinal rods and interbody devices can be used to correct the pre-existing kyphosis and vertebral translational deformity and to provide stability to a treated region. For example, during surgical treatment, interbody implants and spinal pedicle screws with rods can be used to correct abnormal alignment of the spinal vertebrae and provide stability serving to immobilize the spinal motion segment, and with bone graft, can result in a stable fusion. This disclosure describes an improvement over these prior technologies.

SUMMARY

In one embodiment, a method for treating a spine is provided. The method comprises the steps of: pre-operatively measuring a first portion of intervertebral tissue adjacent to a neural foramen; intra-operatively measuring a second portion of the intervertebral tissue adjacent to the neural foramen; generating a threshold value based on the measured portions; and selecting an interbody implant based on the threshold value. In some embodiments, spinal implants, spinal constructs, surgical instruments and systems are provided.

In one embodiment, the method for treating a spine comprises the steps of: pre-operatively measuring at least one dimension of a neural foramen; intra-operatively measuring the at least one dimension; comparing the intra-operative measurement of the at least one dimension with a threshold value; and generating a signal based on the comparison of the measurements and the threshold value.

In one embodiment, the method for treating a spine comprises the steps of: pre-operatively measuring a diameter of a first vertebral body; pre-operatively measuring a diameter of a second vertebral body; providing practitioner selected parameters; generating at least one threshold value based on the measured diameters and the parameters; selecting an interbody implant based on the at least one threshold value; and disposing the interbody implant with an intervertebral disc space.

BRIEF DESCRIPTION OF THE DRAWINGS

The present disclosure will become more readily apparent from the specific description accompanied by the following drawings, in which.

DETAILED DESCRIPTION

Figure 1:
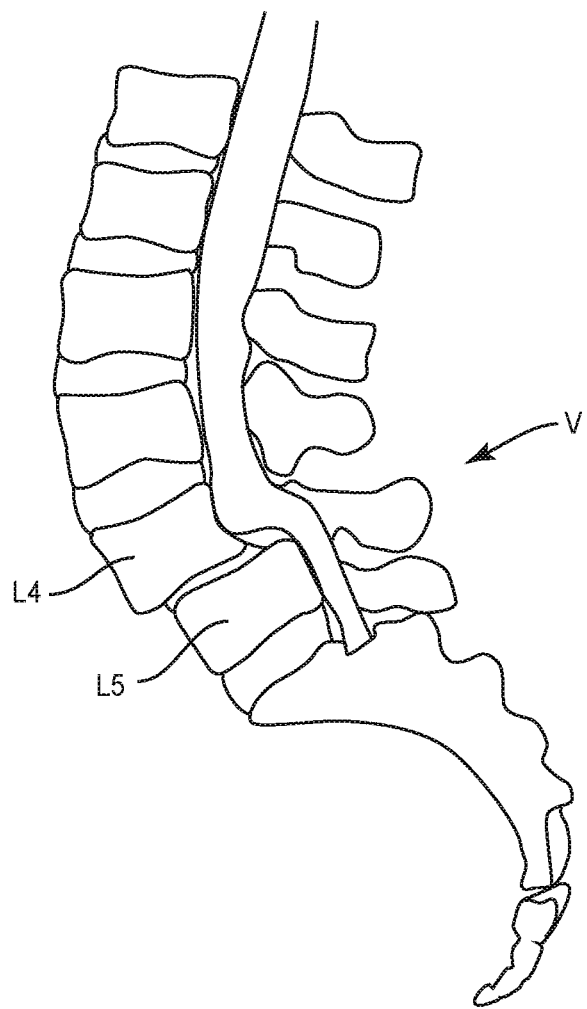
FIG. 1 is a lateral view of a spine to be treated with one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treating a spine. In some embodiments, the systems and methods of the present disclosure are employed with a spinal joint fusion, for example, with a cervical region, a thoracic region, a lumbar region, and/or a sacral region of a spine.

In some embodiments, the present surgical system and method are employed with surgical treatment including a Smith-Petersen osteotomy and/or Ponte-type osteotomy for removal of posterior-most bony structures. In some embodiments, the present surgical system and method are configured to facilitate correction and compress a spine posteriorly with a pedicle-subtraction osteotomy. In some embodiments, the present surgical system and method are employed with surgical treatment including segmental osteotomies followed by posterior compression along unfused regions of a kyphotic deformity. In some embodiments, the present surgical system and method are employed with surgical treatment of Scheuermann's kyphosis and/or coronal deformities, such as adolescent idiopathic scoliosis. In some embodiments, the present surgical system comprises a spinal implant including a hyper-lordotic cage.

In some embodiments, the present surgical system and method are configured to facilitate intra-operative neural foraminal height measurement. In some embodiments, the present surgical system and method measure the spacing of tissue adjacent a neural foramen having a nerve root disposed therewith in connection with surgical treatment to facilitate sagittal alignment, segmental lordosis and/or fusion. In some embodiments, the present surgical system and method facilitates neural foraminal height measurement to achieve segmental lordosis and avoid the influence of pelvic incidence-lumbar lordosis (PI-LL) mismatch and closing of the neural foramen, which can lead to, for example, iatrogenic neural symptoms and nerve root impingement.

In some embodiments, the present surgical system and method measure the spacing of tissue adjacent a neural foramen to determine a selected lordosis of an interbody implant to maintain or improve neural foraminal height or area. In some embodiments, the present surgical system and method measure the spacing of tissue adjacent a neural foramen to intra-operatively determine whether a dimension of the neural foramen has been maintained following a sagittal correction or spondylolisthesis reduction. In some embodiments, the present surgical system and method measure the spacing of tissue adjacent a neural foramen to intra-operatively determine whether the level of indirect decompression has occurred due to an interbody implant spacer. In some embodiments, the present surgical system and method measure the spacing of tissue adjacent a neural foramen to intra-operatively determine the maximum lordotic interbody spacer that can be disposed with a selected vertebral level while maintaining a pre-operative neural foraminal height. In some embodiments, the present surgical system and method provides intra-operative information to prevent re-operations, revision surgery or limit the extensiveness of the intervention in situations where indirect decompression can be confirmed. In some embodiments, the present surgical system and method provides intra-operative information to measure tissue changes for maintaining a pre-operative neural foraminal height.

In some embodiments, the present surgical system and method are employed with a surgical treatment including the step of placing a hyper-lordotic graft with an anterior portion of an intervertebral disc space and performing a Ponte osteotomy posterior to improve lordosis. In some embodiments, the method includes the step of pre-operatively measuring a posterior disc height. In some embodiments, the method includes the step of intra-operatively measuring an anterior disc height, for example, with an interbody trial. In some embodiments, the method includes the step of establishing a lordosis maximum based on the disc heights. In some embodiments, the lordosis maximum is 16.5 angular degrees. In some embodiments, the present surgical system comprises a spinal implant including a hyper-lordotic wedged cage configured to restore a selected lordotic curve to the spine.

In some embodiments, the method includes the step of pre-operatively measuring a neural foramen dimension. In some embodiments, the method includes the step of intra-operatively measuring the neural foramen dimension subsequent to placement of an interbody spacer, for example, with fluoroscopy. In some embodiments, the method includes the step of intra-operatively measuring the neural foramen dimension subsequent to changing the orientation of tissue, for example, with fluoroscopy. In some embodiments, the method includes the step of selecting a threshold value, which in some cases can correspond to a compression warning, alert and/or indicia based on the measured neural foramen dimensions. In some embodiments, the threshold value includes a neural foramen height change, neural foramen area change, dimension range, minimum dimension and/or maximum dimension that generates a signal to provide compression warning, alert and/or indicia. In some embodiments, the threshold value can include a maximum height change of 2 millimeters (mm), In some embodiments, the threshold value can include a maximum area change of 5 $mm^2$. In some embodiments, the threshold value can include a height outside, more than, less than or within a range of 10 mm to 12 mm. In some embodiments, the threshold value can include an area outside, more than, less than or within in a range of 18 $mm^2$ to 23 $mm^2$.

In some embodiments, the present surgical system and method are employed with osteotomy techniques and in connection with achieving incremental lumbar lordosis during posterior degenerative fusion procedures. In some embodiments, the present surgical system and method are employed with a trans-foraminal lumbar interbody fusion (TLIF) for treating spondylolithesis and other degenerative conditions.

In some embodiments, the present surgical system and method are employed with a surgical technique for treating a spine such that an interbody cage is placed in an intervertebral space from a posterior access for creating lordosis. In some embodiments, the present surgical system and method are employed with a method for treating various indications for arthrodesis in a degenerative lumbar spine, such as, for example, a single level lumbar arthrodesis for degenerative lumbar spondylolisthesis, isthmic spondylolisthesis and iatrogenic post-surgical spondylolisthesis, which may include vertebral segments instrumented at any thoracic or lumbar segments, for example, the L4-L5 and L5-S1 inter-vertebral motion segment. In some embodiments, the present surgical system and method are employed to provide improvement in lordosis and/or pelvic parameter ratio, for example, when there is a pre-operative mismatch.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-6, there are illustrated components of a surgical system 10.

The components of surgical system 10 can be fabricated from biologically acceptable materials suitable for medical applications, including metals, synthetic polymers, ceramics and bone material and/or their composites, for example, carbon fiber. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene such as cross-linked polyethylene, ultra-high-molecular-weight polyethylene, high-density polyethylene, vitamin E impregnated polyethylene, low-density polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tricalcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-13), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Surgical system 10 may be employed, for example, with minimally invasive procedures, including percutaneous techniques, mini-open surgical techniques and/or open surgical techniques to pre-operatively and/or intra-operatively measure one or more selected tissue dimensions adjacent a neural foramen, and/or deliver and introduce instrumentation and spinal implants. In some embodiments, one or more components of surgical system 10 facilitate intra-operative neural foraminal measurement of selected dimensions of tissue that defines the neural foramen cavity. In some embodiments, one or more components of surgical system 10 is employed with a method for treating a spine that includes measuring the spacing of tissue adjacent a neural foramen having a nerve root disposed therewith in connection with surgical treatment to facilitate sagittal alignment and segmental lordosis. For example, surgical system 10 measures one or more dimensions of the neural foramen and/or tissue adjacent the neural foramen in connection with achieving segmental lordosis, avoiding the influence of PI-LL mismatch and/or closing of the neural foramen, which can lead to, for example, iatrogenic neural symptoms and nerve root impingement. In some embodiments, surgical system 10 includes medical imaging, as described herein, for measuring one or more dimensions of the neural foramen, and/or adjacent anatomical proxies. In some embodiments, surgical system 10 includes an analog measuring instrument, gauges and/or marked or metered tools, which may include arms, scissors, or protractors having graduated markings, for measuring one or more dimensions of the neural foramen and/or adjacent anatomical proxies.

Figure 2:
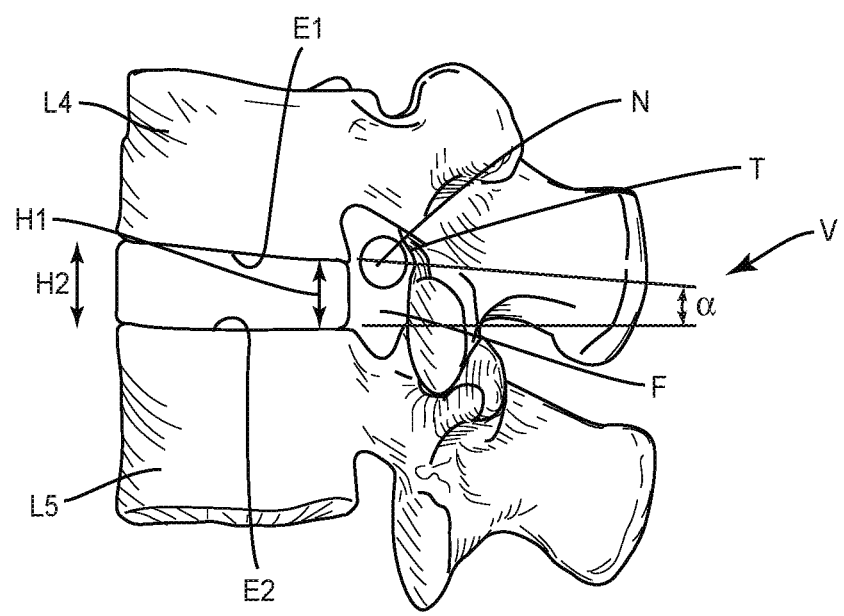
FIG. 2 is a side view of one embodiment of a system in accordance with the principles of the present disclosure disposed with vertebrae.

In one embodiment, as shown in FIGS. 1-6, surgical system 10 is employed to deliver and introduce an interbody implant 12 at a surgical site to vertebrae V within a body of a patient. For example, surgical system 10 is employed with a TLIF surgical approach, technique or procedure, and a method for treating a spine that includes measuring tissue that defines a cavity in bone, such as, for example, a neural foramen F, and/or adjacent anatomical proxies as described herein, between a vertebral body, such as, for example, vertebra L4 and a vertebral body, such as, for example, vertebra L5, as shown in FIG. 2. While some examples shown herein depict L4 and L5 vertebrae, it should be understood that the various embodiments could be used in procedures for the treatment of any selected levels of the human spine, including the cervical spine, thoracic spine and/or lumbar spine including but not limited to the L5-S1 (lumbosacral) disc space. In some embodiments, surgical system 10 is employed with posterior, PLIF, lateral, direct lateral (DLIF), ALIF, OLIF, OLIF25, OLIF51, trans-psoas, anterior, oblique, retroperitoneal, or ante-psoas procedures. In some embodiments, surgical system 10 is employed with a Smith-Petersen osteotomy, Ponte-type osteotomy, chevron-type osteotomy, partial facet joint resection, complete facet joint resection for removal of posterior-most bony structures, as described herein. In some embodiments, surgical system 10 can be employed with various surgical approaches to the spine, including anterior, posterior, posterior mid-line, direct lateral, postero-lateral, and/or antero lateral approaches. These approaches may be done in isolation, sequentially or simultaneously.

Surgical system 10 is employed with the present TLIF surgical procedure such that a patient is positioned in a prone position on a surgical table. Vertebral tissue T defines neural foramen F, which is configured for disposal of nerve root N. A pre-operative measurement of one or more dimensions of neural foramen F including tissue T and/or measurement of an anatomical proxy, is obtained to determine a non-compressed orientation of nerve root N relative to neural foramen F. In some embodiments, the dimensions of neural foramen F can include height, width, diameter, thickness, length, area and/or volume of tissue T and/or neural foramen F. In some embodiments, the dimensions of neural foramen F can include height, width, diameter, thickness, length, area and/or volume of one or more anatomical proxies, such as, for example, an intervertebral disc space between vertebrae, which may include anterior portions and posterior portions thereof, and posterior bony structures such as, facets, pedicles, laminae and processes.

For example, a pre-operative assessment of neural foramen F includes a measurement of an anatomical proxy, such as, for example, an intervertebral disc space S between vertebrae L4 and L5, as shown in FIG. 2. A height H1 of disc space S is measured between an endplate surface E1 and an endplate surface E2 to determine a non-compressed orientation of tissue T of neural foramen F on nerve root N. Height H1 is measured at a posterior portion of disc space S adjacent tissue T of neural foramen F to assess tissue spacing of neural foramen F such that neural foramen F is disposed in a non-compressed orientation and tissue T does not impinge on nerve root N. In some embodiments, height H1 is pre-operatively measured, as described herein, in connection with the present method to avoid PI-LL mismatch in an attempt to attain sagittal alignment of vertebrae V. As such, surgical system 10 is employed to achieve segmental lordosis and resist and/or prevent closing of neural foramen F and resulting compression of nerve root N. In some embodiments, height H1 is measured adjacent a posterior most location of disc space S and endplates E1, E2.

Height H1 is measured with medical imaging, such as, for example, fluoroscopy. In some embodiments, height H1 can be directly measured with measuring instruments, as described herein, from one or more fluoroscopic images displayed from a monitor or radiographic film. In some embodiments, the one or more fluoroscopic images can measure height H1 of the L4-L5 disc space electronically and signals corresponding to the measured height are transmitted to a computer (not shown). Data and/or image transfer of the fluoroscopic images may be performed over a standard video connection or a digital link including wired and wireless. The computer provides the ability to display, via a monitor, as well as save, digitally manipulate, or print a hard copy of the received images. In some embodiments, images may also be displayed to the surgeon through a heads-up display. In some embodiments, measurement of neural foramen F and/or adjacent anatomical proxies can be performed with fluoroscopy.

In some embodiments, medical imaging for measurement of height H1, neural foramen F and/or adjacent anatomical proxies can include x-ray markers, CT, MRI or other imaging techniques, at least one light emitting diode, a wireless component, a wired component, a near field communication component and/or one or more components that generate acoustic signals, magnetic signals, electromagnetic signals and/or radiologic signals.

In some embodiments, medical imaging for measurement of height H1, neural foramen F and/or adjacent anatomical proxies may comprise microsurgical and image guided technologies, such as, for example, a surgical navigation system employing emitters and sensors, which may be employed to track the components of surgical system 10. See, for example, the surgical navigation components and their use, as described in U.S. Pat. Nos. 6,021,343, 6,725, 080 and 6,7969,88, the entire contents of each of these references being incorporated by reference herein. In some embodiments, the surgical navigation system can include an O-arm® imaging device sold by Medtronic Navigation, Inc. having a place of business in Louisville, Colo., USA. In some embodiments, the surgical navigation system can include tracking such as the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein. In some embodiments, surgical system 10 may include a lordosis gauge configured to facilitate determination of a degree of lordosis selected and/or achieved. In some embodiments, the lordosis gauge includes indicia, similar to that described herein, which represents and/or provides information relating to the segmental lordosis of vertebrae L4, L5.

In some embodiments, the pre-operative assessment of neural foramen F includes a measurement of an anatomical proxy, such as, for example, a height H2 of disc space S, as shown in FIG. 2, similar to height H1 described herein. Height H2 is measured at an anterior portion of disc space S adjacent tissue T of neural foramen F to assess tissue spacing of neural foramen F such that neural foramen F is disposed in a non-compressed orientation and tissue T does not impinge on nerve root N. In some embodiments, height H2 is measured adjacent an anterior most location of disc space S and endplates E1, E2. Height H2 is measured with medical imaging, such as, for example, fluoroscopy, similar to that described herein with regard to height H1. In some embodiments, height H2 can be directly measured with measuring instruments, as described herein, from one or more fluoroscopic images displayed from a monitor or radiographic film. In some embodiments, the one or more fluoroscopic images can measure height H2 electronically and signals corresponding to the measured height are transmitted to a computer (not shown), similar to that described herein. In some embodiments, the pre-operative measurements H1, H2 are utilized to determine and/or calculate a pre-operative lordosis a of vertebrae L4, L5 and/or adjacent vertebral levels, for example, via an algorithm, as described herein.

In connection with the TLIF procedure, a medical practitioner makes and/or creates an incision in tissue, which includes soft tissue and/or muscle, to obtain access to a surgical site including vertebral levels L4, L5. In some embodiments, a retractor (not shown) is inserted through the incision and disposed with the tissue. The retractor engages and spaces the tissue to create a surgical pathway and/or opening to the surgical site, which includes a surgical pathway employed with the TLIF surgical approach.

Figure 3:
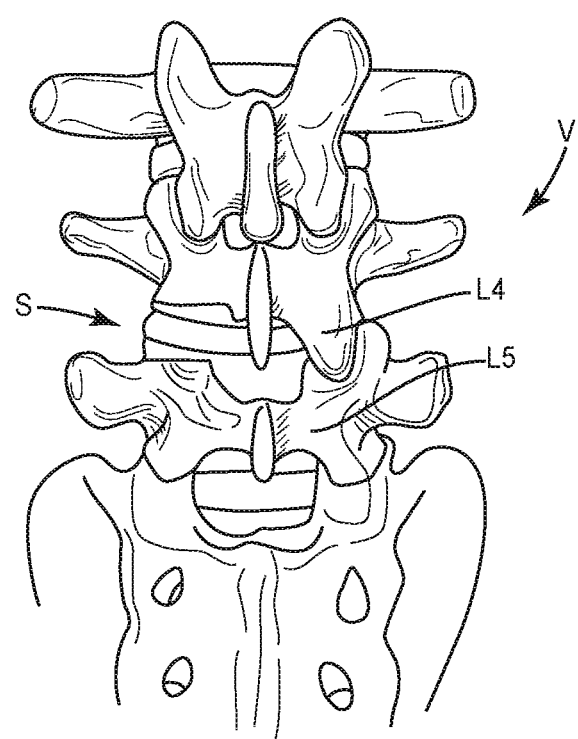
FIG. 3 is a plan view of the spine shown in FIG. 1.
Figure 4:
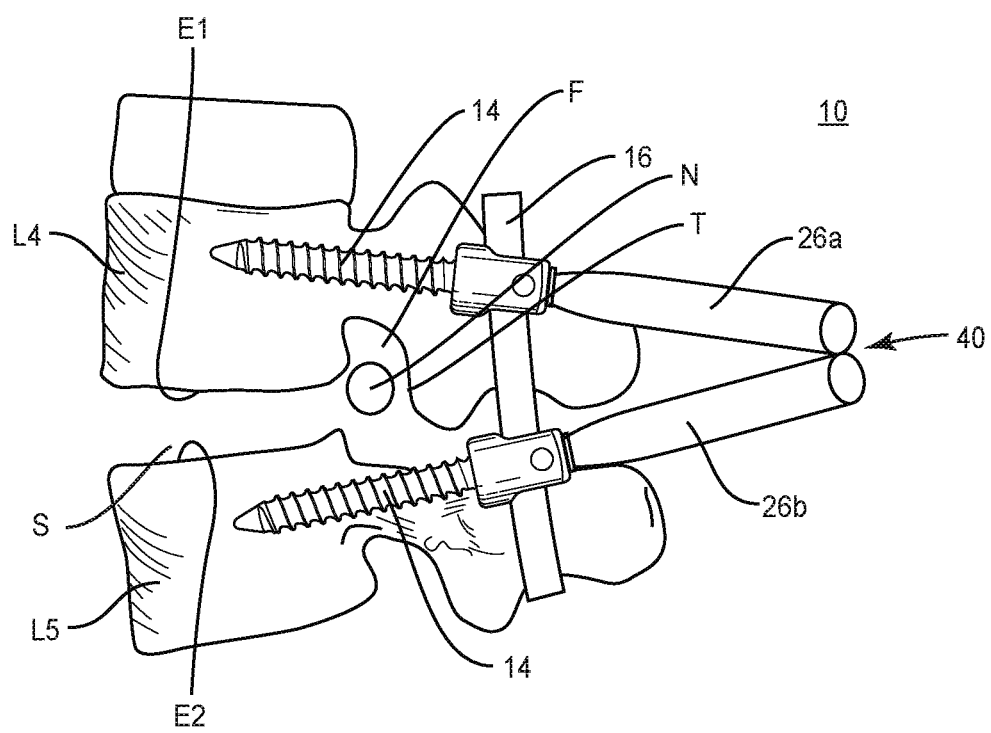
FIG. 4 is a side view of components of one embodiment of a system in accordance with the principles of the present disclosure disposed with vertebrae.

Once access to the surgical site is obtained, a surgical procedure, as described herein, is performed for treating the spine disorder. The diseased and/or damaged portion of vertebrae V, which may include diseased and/or damaged intervertebral disc tissue, are removed to create a vertebral space between vertebrae L4, L5. A preparation instrument can be employed to remove disc tissue, fluids, adjacent tissues and/or bone, and scrape and/or remove tissue from endplate surfaces E1, E2. Vertebral facets, such as, for example, an L4 inferior facet and an L5 superior facet are resected, as shown in FIGS. 3 and 4. In some embodiments, a trans-foraminal discectomy is performed to create space S between vertebral bodies L4, L5.

In some embodiments, sequential trial implants 20 are delivered to and used to distract space S and apply appropriate tension in the L4-L5 intervertebral space allowing for indirect decompression. Various trials 20 are utilized to achieve the desired lordosis. In some embodiments, a resection of pedicles is conducted for further posterior compression to achieve a contact between endplates E1, E2 and the superior and inferior portions of interbody implant 12.

In some embodiments, pilot holes are made in selected vertebra of vertebrae V for receiving a surgical instrument 40, as shown in FIG. 4, employed to manipulate vertebrae L4, L5. In some embodiments, spinal constructs including rods are employed as provisional and/or working rods to support vertebrae V during a surgical procedure. In some embodiments, surgical system 10 may include one or a plurality of the spinal constructs. In some embodiments, the plurality of spinal constructs may be disposed in various alternate orientations, such as, for example, side by side, parallel, transverse and/or other angular orientations such as acute or obtuse, co-axial and/or may be offset or staggered. In some embodiments, the plurality of spinal constructs may provide a template configuration for permanently implantable spinal rods, such as, implantable, final, permanent, removable, non-removable, bio-absorbable, resorbable and/or bio-degradable, and/or comprise permanently implantable spinal rods.

Surgical instrument 40 includes lever arms, such as, for example, extenders 26a, 26b. Extenders 26a, 26b are attached with bone screws 14 to manipulate vertebrae L4, L5. Surgical instrument 40 manipulates vertebrae L4, L5. As such, surgical instrument 40 manipulates vertebrae L4, L5 to selectively rotate vertebrae L4, L5 about trial 20 to facilitate determination of the configuration and dimension of interbody implant 12 and achieve segmental lordosis of vertebrae L4, L5. In some embodiments, surgical system 10 may comprise various surgical instruments, such as, for example, drivers, reducers, spreaders, distractors, blades, clamps, forceps, elevators and drills, which may be alternately sized and dimensioned, and arranged as a kit.

An intra-operative measurement, similar to the pre-operative measurement described herein, of one or more dimensions of neural foramen F including tissue T and/or measurement of an anatomical proxy, is obtained to determine a selected configuration and dimension of an interbody implant 12 during insertion of trials 20. The pre-operative measurement and the intra-operative measurement facilitate determination of an interbody implant 12 having a selected lordosis to maintain a non-compressed orientation of nerve root N relative to neural foramen F, as described herein. In some embodiments, the selected lordosis can include or can be based on an angular representation of a lordosis maximum, a lordosis minimum and/or a range of lordosis. In some embodiments, the selected lordosis can be determined based on a selected difference of an angular representation of pelvic incidence, measured relative to a hip axis, relative to an angular representation of lumbar lordosis.

Figure 5:
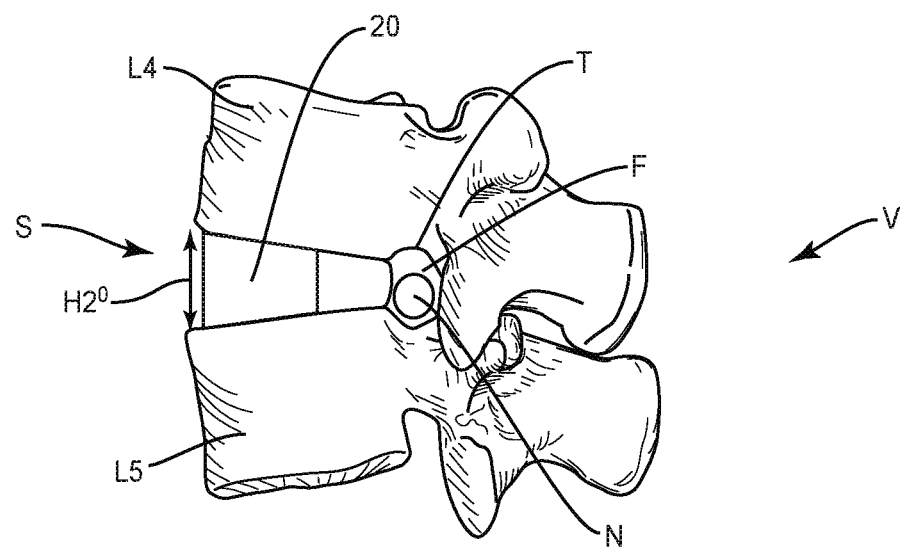
FIG. 5 is a side view of one embodiment of a system in accordance with the principles of the present disclosure disposed with vertebrae.

For example, an intra-operative assessment of neural foramen F includes a measurement of an anatomical proxy, such as, for example, a height H2$^O$ of disc space 5, as shown in FIG. 5. Height H2$^O$ is measured between endplate surfaces E1, E2 to determine a selected configuration and dimension of an interbody implant 12 to maintain a non-compressed orientation of tissue T of neural foramen F on nerve root N. Height H2$^O$ is measured at an anterior portion of disc space S adjacent tissue T of neural foramen F to assess tissue spacing of neural foramen F such that neural foramen F is disposed in a non-compressed orientation and tissue T does not impinge on nerve root N. In some embodiments, height H2$^O$ is intra-operatively measured, as described herein, in connection with the trialing methods and trial implants 20, as described herein. In some embodiments, height H2$^O$ is intra-operatively measured, as described herein, in connection with the present method to avoid PI-LL mismatch in an attempt to attain sagittal alignment. As such, surgical system 10 is employed to achieve segmental lordosis and resist and/or prevent closing of neural foramen F and resulting compression of nerve root N. In some embodiments, height H2° is measured adjacent an anterior most location of disc space S and endplates E1, E2. In some embodiments, height H2° can be measured at one or more selected locations along disc space S between an anterior most and a posterior most location thereof and endplates E1, E2.

Figure 6:
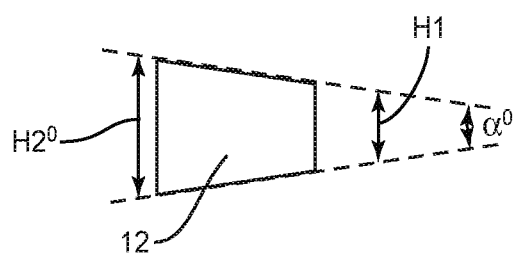
FIG. 6 is a side view of components of one embodiment of a system in accordance with the principles of the present disclosure.

Height H2° is measured with medical imaging, such as, for example, fluoroscopy, similar to that described herein with regard to heights H1, H2. In some embodiments, height H2° can be directly measured with measuring instruments, as described herein, from one or more fluoroscopic images displayed from a monitor or radiographic film. In some embodiments, the one or more fluoroscopic images can measure height H2° electronically and signals corresponding to the measured height are transmitted to a computer (not shown), similar to that described herein. The pre-operative and intra-operative measurements H1, H2 and/or H2° are utilized to determine and/or calculate at least one threshold value, such as, for example, a selected lordosis, as described herein, of an interbody implant 12 to maintain a non-compressed orientation of tissue T of neural foramen F on nerve root N. The threshold value includes a selected lordosis of vertebrae L4, L5 and/or adjacent vertebral levels, and/or one or more selected angular orientations α° of interbody implant 12, as shown in FIG. 6, to facilitate achieving the lordosis with the vertebral engaging surfaces of interbody implant 12. In some embodiments, the threshold value includes a selected range of lordosis of vertebrae L4, L5 and/or adjacent vertebral levels, and/or one or more selected angular orientations α° of interbody implant 12 in a range of 5 through 40 degrees. In some embodiments, the threshold value includes a selected range of lordosis of vertebrae L4, L5 and/or adjacent vertebral levels, and/or one or more selected angular orientations α° of interbody implant 12 in a range of 10 through 25 degrees. In some embodiments, the threshold value includes a selected maximum lordosis of vertebrae L4, L5 and/or adjacent vertebral levels, and/or one or more selected angular orientations α° of interbody implant 12 of 0, 6, 12, 16.5 or 18 degrees.

The components of surgical system 10 and the present method include an algorithm and/or formula that utilizes parameters, for example, pre-operative and intra-operative measurements H1, H2 and/or H2°, and/or practitioner selected parameters, to determine and/or calculate one or more threshold values, as described herein. For example, the algorithm and/or formula utilizes measurements H1, H2 and/or H2°, and/or practitioner selected parameters, to determine and/or calculate a selected lordosis of vertebrae L4, L5 and/or adjacent vertebral levels, and/or one or more selected angular orientations α° of interbody implant 12, as described herein. In some embodiments, the algorithm and/or formula comprises the calculation of angle α° based on a pre-operative measurement of H1 and H2 at selected locations of disc space S, and/or practitioner selected parameters, as described herein. A subsequent surgical intervention includes expanding H2 with trial 20, as described herein, to H2°. A selected angular orientation of the vertebral engaging surfaces of interbody implant 12, angle α°, is calculated using H1, H2 and H2° at the selected locations. An interbody implant 12 having one or more threshold values and/or practitioner selected parameters is selected using measurements H1, H2, H2° and α°.

In some embodiments, the computer of surgical system 10 includes a computer readable medium for storing an algorithm and/or methods that utilize pre-operative and intra-operative measurements H1, H2 and/or H2°, and/or practitioner selected parameters, to determine and/or calculate one or more threshold values, as described herein, and may include software programs, applications and codes for determining treatment including selection of the configuration and dimension of interbody implant 12, for example, a selected lordosis of the vertebral engaging surfaces of interbody implant 12. Such software programs, applications and codes being readily prepared by one skilled in the art based on the present disclosure, to be executed by a computer processor of surgical system 10. The processor executes the algorithm to determine the threshold value based on measurements H1, H2 and/or H2°, and/or practitioner selected parameters. The computer includes a user interface or monitor that provides indicia of the threshold value, for example, a numerical representation/display of a selected lordosis of the vertebral engaging surfaces of interbody implant 12. In some embodiments, the indicia may include human readable visual indicia, human readable tactile indicia and/or audible indicia provided by the computer. In some embodiments, the indicia may include an analog, such as, for example, a dial with a numerical indicator of angle and/or digital display, such as, for example, LED and/or LCD.

In some embodiments, a size of interbody implant 12 is selected after trialing and determination of one or more threshold values. In some embodiments, interbody implant 12 is visualized by fluoroscopy and oriented before introduction into vertebral space S. Interbody implant 12 is selected based on one or more threshold values in connection with the present method to achieve segmental lordosis, avoid PI-LL mismatch in an attempt to attain sagittal alignment, and to resist and/or prevent closing of neural foramen F and resulting compression of nerve root N, as described herein. An inserter (not shown) is attached with interbody implant 12 to deliver interbody implant 12 adjacent to a surgical site for implantation adjacent the L4-L5 intervertebral space. In some embodiments, algorithm calculations, and pre-operative and intra-operative measurements H1, H2 and/or H2° and/or α°, and/or practitioner selected parameters, can be utilized with a surgical procedure, and/or intra-operative modification/adjustment to dispose interbody implant 12 at one or more selected locations along disc space S between an anterior most and a posterior most location thereof and endplates E1, E2. For example, interbody implant 12 can be implanted with an anterior most, mid-body or a posterior most location of disc space S.

In some embodiments, the described pre-operative measurements are acquired and change at a time of the surgical procedure, such as, for example when a patient is positioned prone on the OR table. In some embodiments, pre-operative measurements can be recalculated to account for these variations. In some embodiments, one or more of the algorithms, as described herein, performs calculations to account for these changes and maps back to the original pre-operative strategy and/or practitioner selected parameters, as described herein. In some embodiments, the algorithm calculations reconcile the pre-operative strategy with the prone patient positioning via an overlay or assessment of the strategy versus real time prone position. In some embodiments, the real time anatomy position may be obtained by medical imaging. In some embodiments, the algorithm calculations are configured to modify and/or assess the pre-operative strategy in the OR versus the prone patient positioning via a rescan and/or registration process that takes the pre-operative strategy and indicates how measurements have changed on the table relative to the pre-operative strategy. In some embodiments, a practitioner may confirm and/or modify the strategy based on real time data. For example, in some embodiments, a pre-operative measurement of height H1 is 7 mm, height H2 is 8 mm and an angle α of 2 degrees. When the patient is disposed in a prone position or on the OR table, height H1 is 9 mm, H2 remains 8 mm and angle α becomes −2 degrees, this information would provide information to adjust the procedure type and extent.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiopaque markers may be included for identification under x-ray, fluoroscopy, CT, MRI or other imaging techniques.

In some embodiments, surgical system 10 may include one or a plurality of interbody implants, rods, tethers, plates, connectors and/or bone fasteners connectable with vertebrae V for treatment of the L4-L5 vertebrae and/or for use with a single vertebral level or a plurality of vertebral levels of vertebrae V. In some embodiments, surgical system 10 may include one or a plurality of bone fasteners that may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 10 includes an agent, which may be disposed, packed, coated or layered within, on, adjacent or about the components and/or surfaces of surgical system 10, and/or disposed with tissue. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 7-12, surgical system 10, similar to the systems and methods described herein, is employed with a surgical procedure, as described herein, for treating a spine of a patient and includes an algorithm and/or formula that calculates one or more threshold values, similar to that described herein, based on one or more practitioner selected parameters, such as, for example, a planned anterior height correction $H2^P$, a planned lordosis correction $\alpha^P$, a planned implant placement $D3^P$ and pre-operative measurements.

Figure 7:
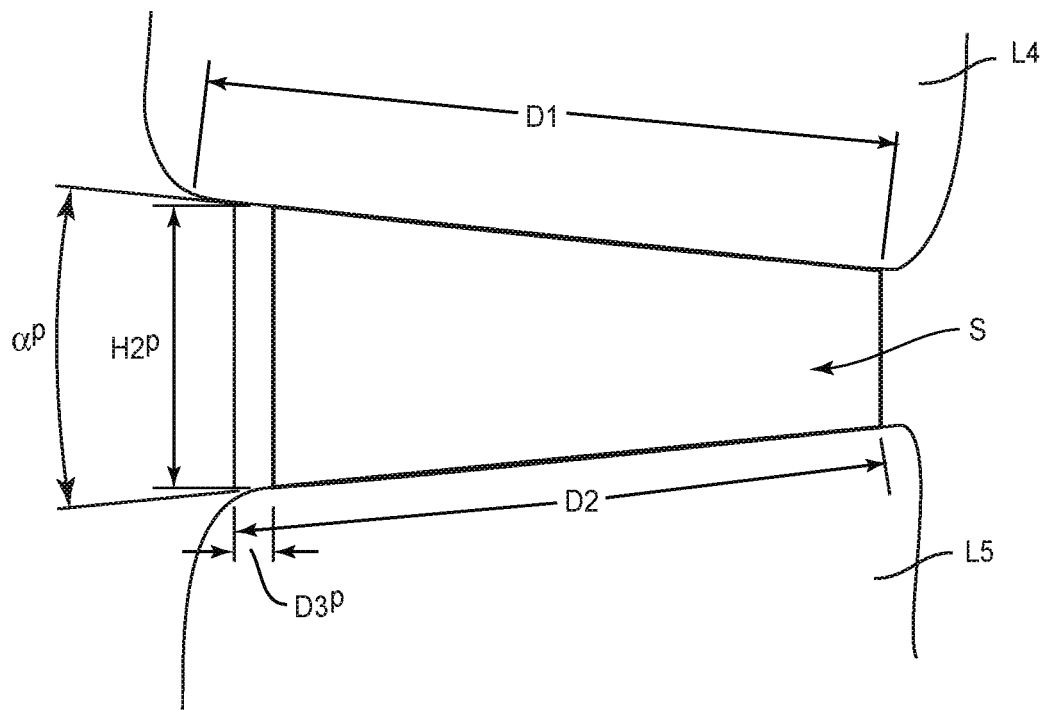
FIG. 7 is a side view of vertebrae.

Pre-operative assessment of neural foramen F, similar to that described herein, includes measurement of anatomical proxies including a sagittal diameter D1 of a superior vertebral body L4 and a sagittal diameter D2 of an inferior vertebral body L5, as shown in FIG. 7. For example, diameter D1=34.0 mm and diameter D2=32.0 mm, as measured via medical imaging, similar to that described herein. Practitioner selected parameters include a planned anterior height correction $H2^P$=14.0 mm, a planned lordosis correction $\alpha^P$=12 angular degrees and a planned implant placement $D3^P$=2.0 mm.

Figure 9:
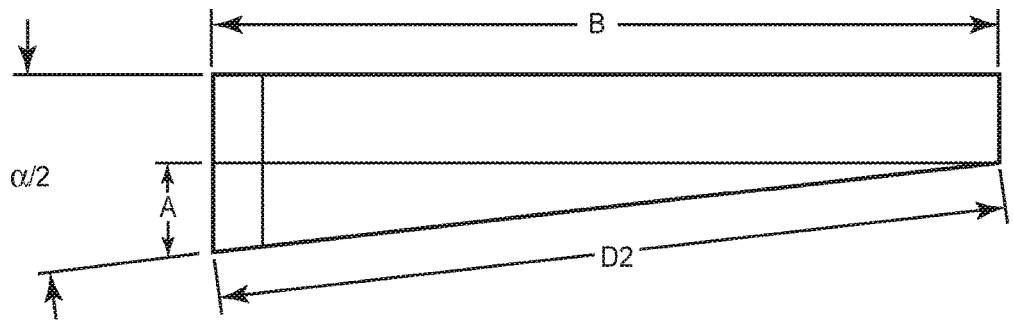
FIG. 9 is a diagram illustrating algorithm parameters of one embodiment of a system in accordance with the principles of the present disclosure.
Figure 10:
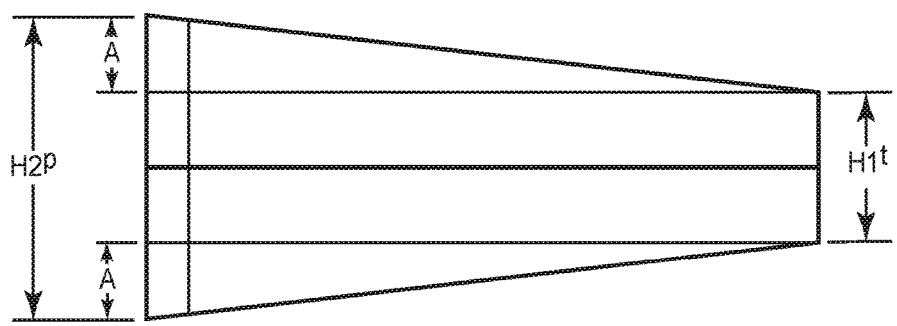
FIG. 10 is a diagram illustrating algorithm parameters of one embodiment of a system in accordance with the principles of the present disclosure.

The present algorithm calculates a threshold value, posterior height Hit of intervertebral space S, in connection with selection of an interbody implant 12 for disposal with intervertebral space S. The present algorithm includes a comparison of the diameter D1 value relative to the diameter D2 value to determine the lesser value. In this example, D1=34.0 mm>D2=32.0 mm. As such, D2 has the lesser value and can be used as a limit relating to implant depth. Posterior height $H1^t$ is calculated with the present algorithm based on the parameters and measurements, as shown in FIGS. 9 and 10, using formulas, as follows:

1) Divide planned lordosis correction $\alpha^P$ by 2, $\alpha^P$=12/2=6 degrees; and convert to radians,
$\alpha^P$/2=0.10472 radians.

2) Calculate A and B lengths of a right triangle;

a. $A=32*\sin(0.10472)=3.3$ mm b. $B=32*\cos(0.10472)=31.8$ mm

3) Posterior height $H1^t=H2^P-2*A=14-2*3.3=7.3$ mm

Figure 11:
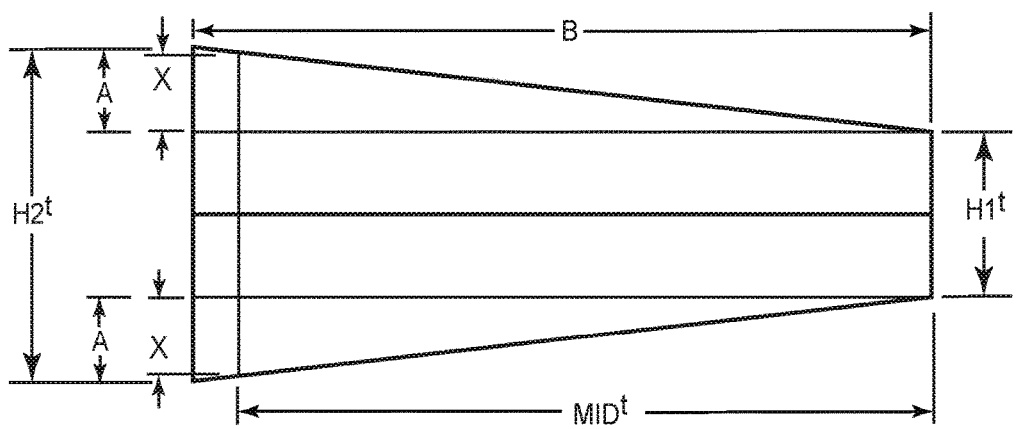
FIG. 11 is a diagram illustrating algorithm parameters of one embodiment of a system in accordance with the principles of the present disclosure.

The present algorithm calculates a threshold value, an implant height $H2^t$, in connection with selection of an interbody implant 12 for disposal with intervertebral space S. Implant height $H2^t$ is calculated with the present algorithm based on the parameters and measurements, as shown in FIG. 11, using formulas, as follows:

1) Calculate length X of a right triangle:

a. $X=(B-D3^P)*(A/B)=(31.8-2.0)*(3.3-31.8)=3.13$ mm

2) Implant height $H2^t=H1^t+2*X=7.3+2*3.13=13.6$ mm

Figure 12:
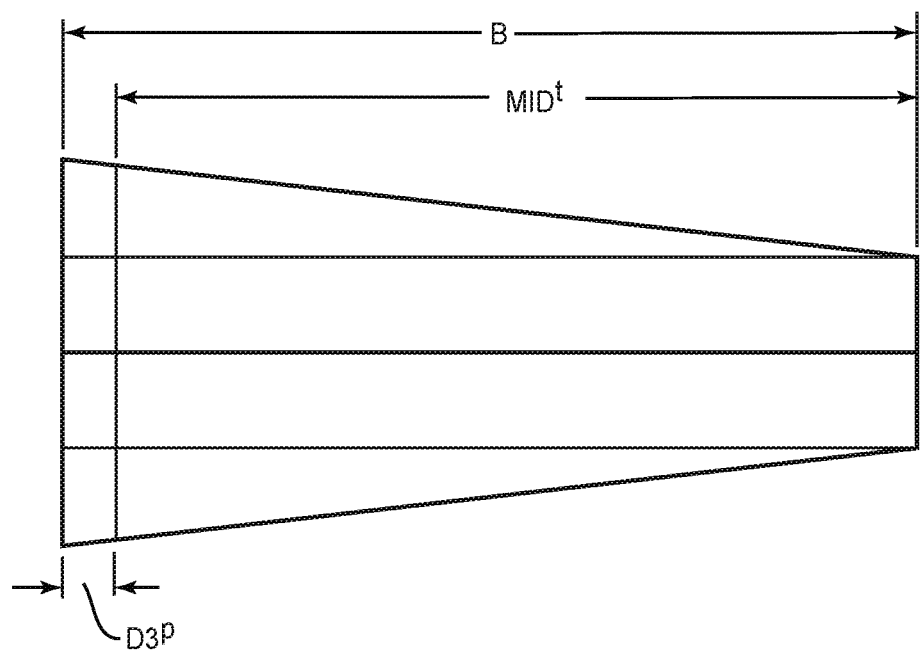
FIG. 12 is a diagram illustrating algorithm parameters of one embodiment of a system in accordance with the principles of the present disclosure.

The present algorithm calculates a threshold value, a maximum implant depth $MID^t$, in connection with selection of an interbody implant 12 for disposal with intervertebral space S, Maximum implant depth $MID^t$ is calculated with the present algorithm based on the parameters and measurements, as shown in FIG. 12, using a formula, as follows:

1) $MID^t=B-D3^P=31.8-2.0=29.8$ mm

Figure 8:
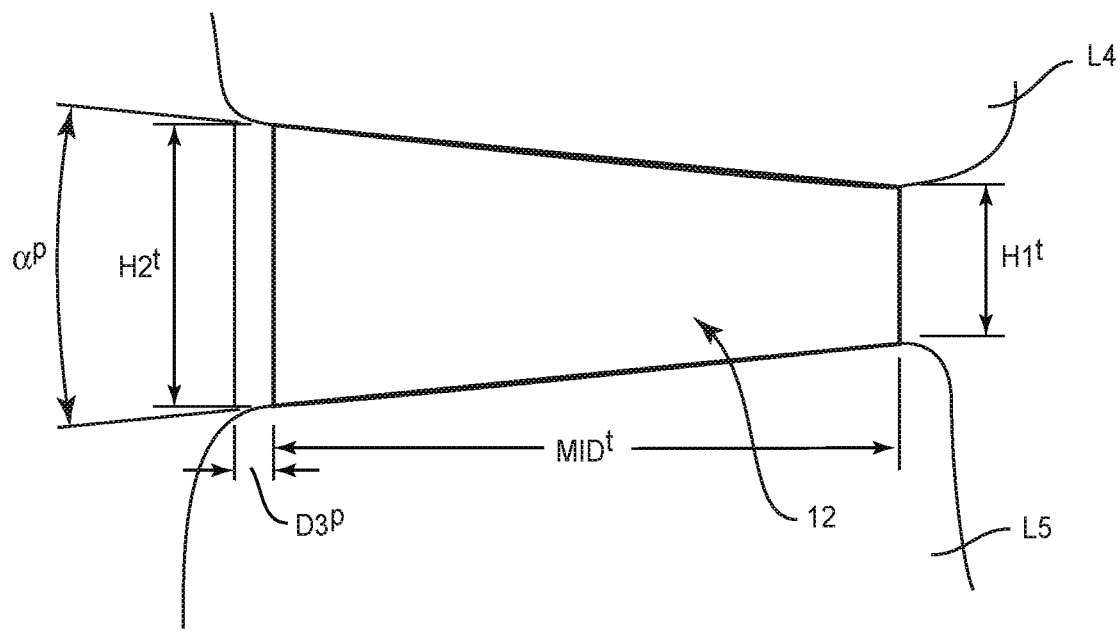
FIG. 8 is a side view of components of one embodiment of a system in accordance with the principles of the present disclosure disposed with vertebrae.

The present method including threshold values, $H1^t$, $H2^t$, $MID^t$ calculated above with the present algorithm are employed for selecting an interbody implant 12, as shown in FIG. 8. For example, an interbody implant 12, as described herein, is selected, based on the present method employing the algorithm, having an implant height of 13.6 mm, a lordosis of 12 degrees and a maximum implant depth of less than 29.8 mm.

In one embodiment, as shown in FIGS. 13-18, surgical system 10, similar to the systems and methods described herein, is employed with a surgical procedure, as described herein, for treating a spine of a patient and includes an algorithm and/or formula that calculates one or more threshold values, similar to that described herein, based on one or more practitioner selected parameters, such as, for example, a planned posterior height correction $H1^P$, a planned lordosis correction $\alpha^P$, a planned implant placement $D3^P$ and pre-operative measurements.

Figure 13:
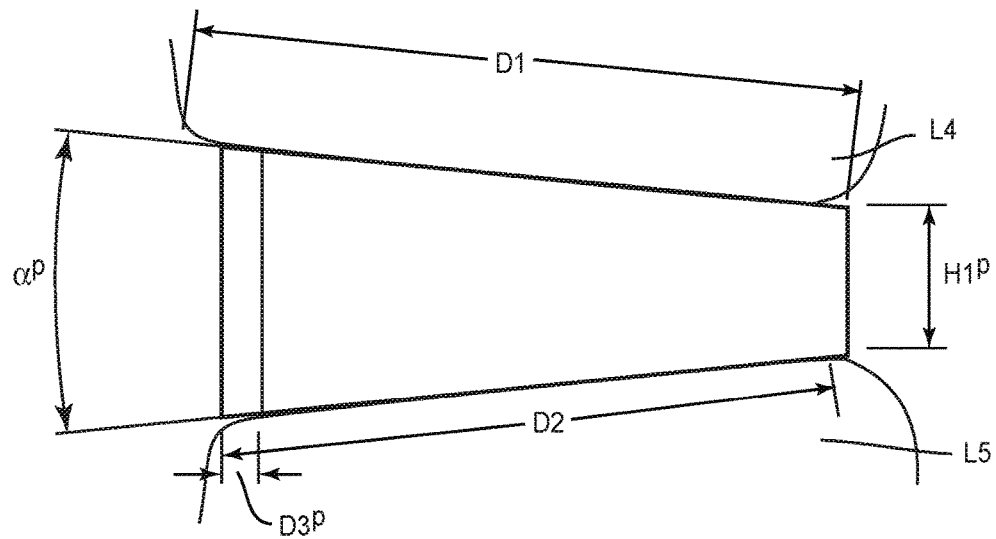
FIG. 13 is a diagram illustrating algorithm parameters of one embodiment of a system in accordance with the principles of the present disclosure.

Pre-operative assessment of neural foramen F, similar to that described herein, includes measurement of anatomical proxies including a sagittal diameter D1 of a superior vertebral body L4 and a sagittal diameter D2 of an inferior vertebral body L5, as shown in FIG. 13. For example, diameter D1=34.0 mm and diameter D2=32.0 mm, as measured via medical imaging, similar to that described herein. Practitioner selected parameters include a planned posterior height correction $H1^P$=7.3 mm, a planned lordosis correction $\alpha^P$=12 angular degrees and a planned implant placement $D3^P$=2.0 mm.

Figure 14:
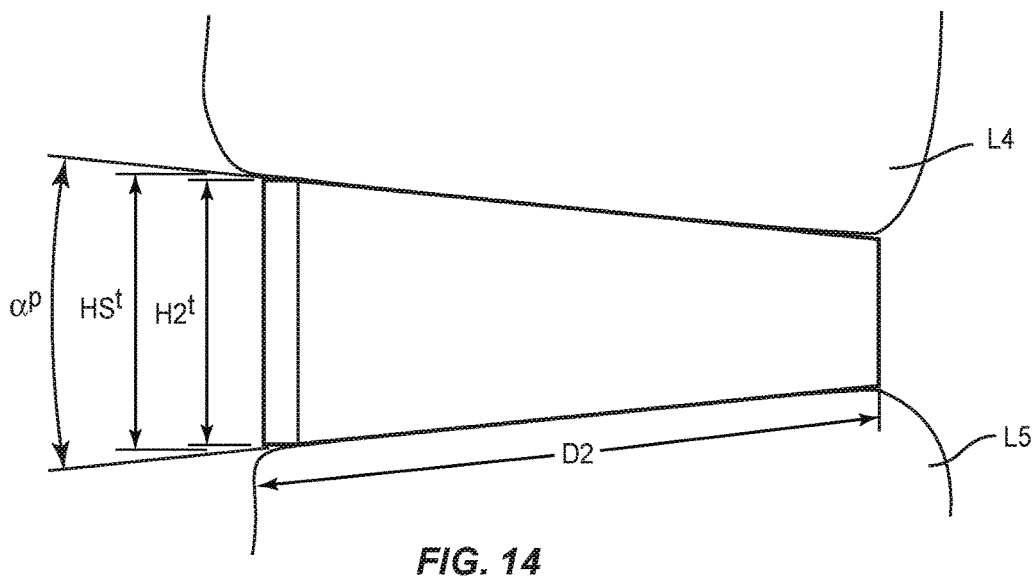
FIG. 14 is a diagram illustrating algorithm parameters of one embodiment of a system in accordance with the principles of the present disclosure.
Figure 15:
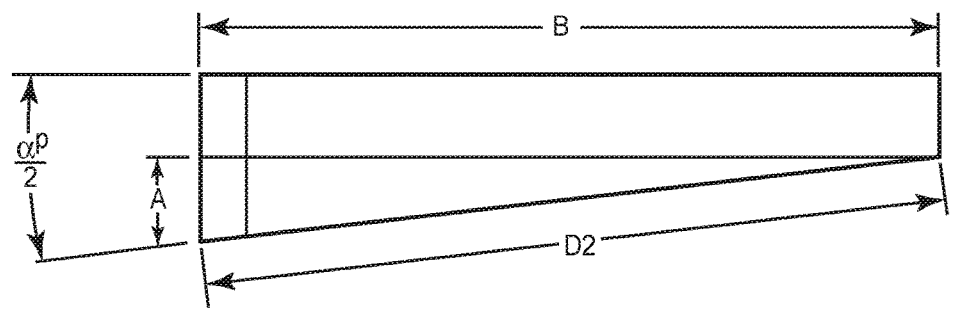
FIG. 15 is a diagram illustrating algorithm parameters of one embodiment of a system in accordance with the principles of the present disclosure.

The present algorithm calculates a threshold value, anterior height $HS^t$ of intervertebral space S, in connection with selection of an interbody implant 12 for disposal with intervertebral space S. The present algorithm includes a comparison of the diameter D1 value relative to the diameter D2 value to determine the lesser value. In this example, D1=34.0 mm>D2=32.0 mm. As such, D2 has the lesser value and can be used as a limit relating to implant depth. Anterior height $HS^t$ is calculated with the present algorithm based on the parameters and measurements, as shown in FIGS. 14 and 15, using formulas, as follows:

1) Divide planned lordosis correction $\alpha^P$ by 2, $\alpha^P$=12/2=6 degrees 2) Convert to radian, $\alpha^P/2$=0.10472 radians.

3) Calculate A and B lengths of a right triangle:

a. $A$=32*sin(0.10472)=3.3 mm b. $B$=32*cosin(0.10472)=31.8 mm

4) Anterior height $HS^t = H1^2 + 2*A = 7.3 + 2*3.3 = 14.0$ mm

Figure 16:
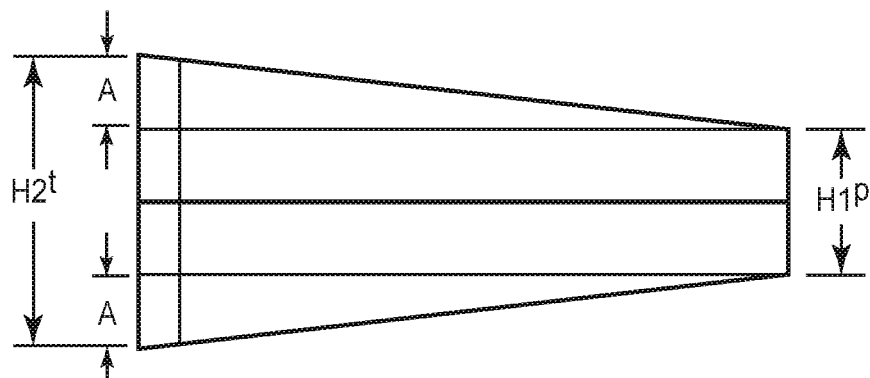
FIG. 16 is a diagram illustrating algorithm parameters of one embodiment of a system in accordance with the principles of the present disclosure.

The present algorithm calculates a threshold value, an implant height $H2^t$, in connection with selection of an interbody implant 12 for disposal with intervertebral space S. Implant height $H2^t$ is calcuted with the present algorithm based on the parameters and measurements, as shown in FIG. 16, using formulas, as follows:

1) Calculate length X of a right triangle:

a. $X=(B-D3^P)*(A/B)=(31.8-2.0)*(3.3-31.8)=3.13$ mm

2) Implant height $H2^t = H1^t + 2*X = 7.3 + 2*3.13 = 13.6$ mm

Figure 17:
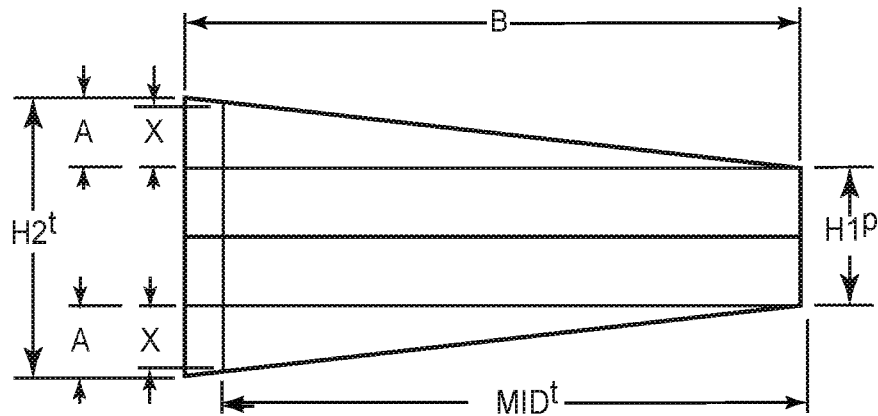
FIG. 17 is a diagram illustrating algorithm parameters of one embodiment of a system in accordance with the principles of the present disclosure.

The present algorithm calculates a threshold value, a maximum implant depth $MID^t$, in connection with selection of an interbody implant 12 for disposal with intervertebral space S. Maximum implant depth $MID^t$ is calculated with the present algorithm based on the parameters and measurements, as shown in FIG. 17, using a formula, as follows:

1) $MID^t = B - D3^P = 31.8 - 2.0 = 29.8$ mm

Figure 18:
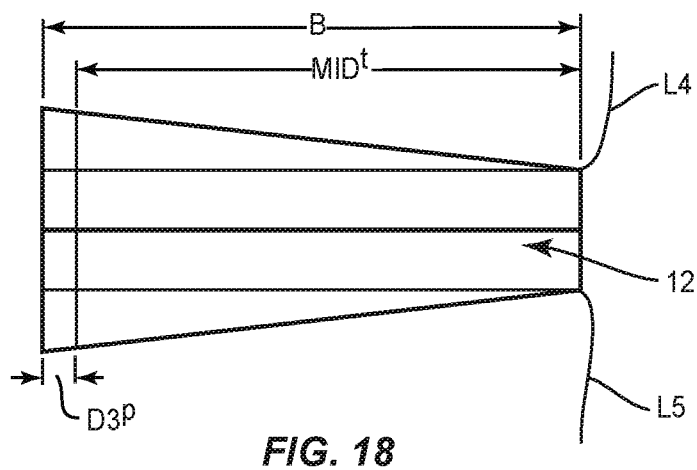
FIG. 18 is a diagram illustrating algorithm parameters of one embodiment of a system in accordance with the principles of the present disclosure.

The present method including threshold values, $HS^t$, $H2^t$, $MID^t$ calculated above with the present algorithm are employed for selecting an interbody implant 12, as shown in FIG. 18. For example, an interbody implant 12, as described herein, is selected, based on the present method employing the algorithm, having an implant height of 13.6 mm, a lordosis of 12 degrees and a maximum implant depth of less than 29.8 mm.

Figure 19:
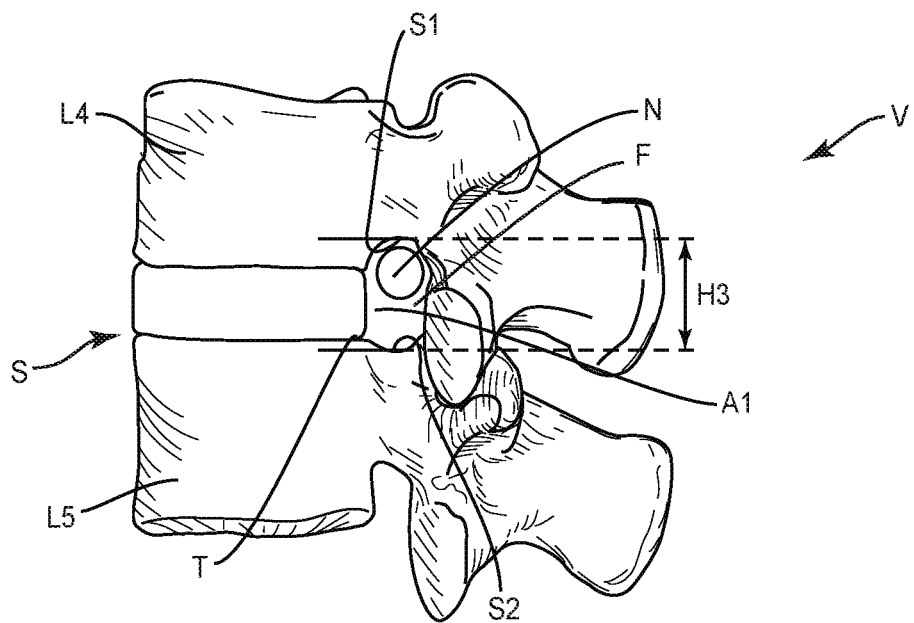
FIG. 19 is a side view of vertebrae.
Figure 20:
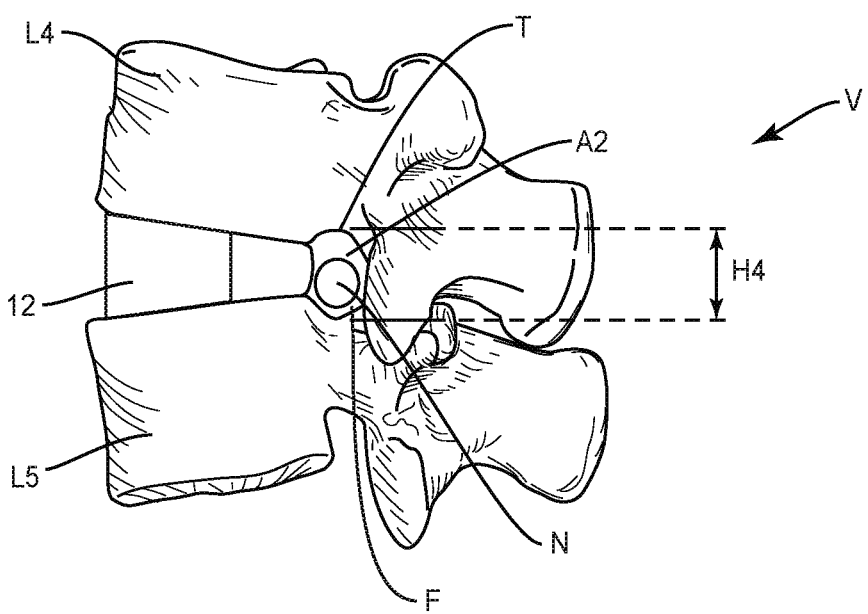
FIG. 20 is a side view of components of one embodiment of a system in accordance with the principles of the present disclosure disposed with vertebrae.

In one embodiment, as shown in FIGS. 19 and 20, surgical system 10, similar to the systems and methods described herein, is employed with a surgical procedure, as described herein, for treating a spine of a patient and includes an algorithm and/or formula that calculates one or more threshold values based on one or more practitioner selected parameters, similar to that described with regard to FIGS. 1-18.

A pre-operative measurement of neural foramen F includes measurement of a height H3 of neural foramen F taken between a superior surface S1 and an inferior surface 32, as shown in FIG. 19. Surfaces S1, S2 include portions of tissue T that define the cavity of neural foramen F and height H3 is measured to assess tissue spacing of neural foramen F such that neural foramen F is disposed in a non-compressed orientation and tissue T does not impinge on nerve root N.

Height H3 is measured with medical imaging, similar to that described herein. In some embodiments, one or more fluoroscopic images measure height H3 of the L4-L5 disc space electronically and signals corresponding to the measured height are transmitted to a computer, similar to that described herein.

In some embodiments, a pre-operative measurement of neural foramen F includes a measurement of an area A1 of neural foramen F, as shown in FIG. 19, Area A1 is defined by the surfaces of tissue T, in one or a plurality planes that include neural foramen F, and area A1 is measured to assess tissue spacing of neural foramen F such that neural foramen F is disposed in a non-compressed orientation and tissue T does not impinge on nerve root N. In some embodiments, medical imaging, for example, CT, MRI or surgical navigation, as described herein, is employed to pre-operatively measure area A1 and/or a volume of neural foramen F.

In connection with the TLIF procedure, access to the surgical site is obtained, as described herein, and diseased and/or damaged portions of vertebrae V are removed to create space S between vertebrae L4, L5, Posterior bony structures can be removed and sequential trial implants 20 are delivered to and used to distract space S and apply appropriate tension in the L4-L5 intervertebral space allowing for indirect decompression. Various trials 20 are utilized to achieve the desired lordosis, Surgical instrument 40 is employed to manipulate vertebrae L4, L5, similar to that described herein.

An intra-operative measurement of a height H4 and/or an area A2, as shown in FIG. 20, similar to the pre-operative measurement of height H3 and area A1 described herein, of neural foramen F is obtained to determine a selected surgical treatment and/or configuration and dimension of an interbody implant 12 during insertion of trials 20. The pre-operative measurement and the intra-operative measurement facilitate determination of an interbody implant 12 having a selected lordosis to maintain a non-compressed orientation of nerve root N relative to neural foramen F, similar to that described herein. During manipulation of the L4-L5 vertebrae and/or trialing, height H4 and/or area A2, are measured to assess tissue spacing of neural foramen F such that neural foramen F is disposed in a non-compressed orientation and tissue T does not impinge on nerve root N. In some embodiments, height H4 and/or area A2 are intra-operatively measured, as described herein, in connection with the present method to avoid PI-LL mismatch in an attempt to attain sagittal alignment. Height H4 and/or area A2 are measured with medical imaging, as described herein, and signals corresponding to the measured height are transmitted to the computer, similar to that described herein.

In some embodiments, the difference between pre-operative height H3 and intra-operative height H4 is determined and/or calculated, and compared to one or more threshold values, which correspond to a selected maximum and/or selected range of lordosis, relative to pre-operative height H3, of an interbody implant 12 to maintain a non-compressed orientation of tissue T of neural foramen F on nerve root N. The threshold value corresponds to a selected lordosis having one or more selected angular orientations of vertebral engaging surfaces of interbody implant 12, similar to that described herein. In one example, height H3 is 12 mm and the selected threshold value, which corresponds to a selected maximum and/or selected range of lordosis, relative to pre-operative measurement H3, is 2 mm. Height H4 is intra-operatively measured and compared to height H3. The difference of H3, H4 is compared to the threshold value. A difference greater than 2 mm is outside the selected range of lordosis and a difference of less than 2 mm is within the selected range of lordosis. For example, if manipulation of vertebrae V and/or trialing provides a height H4 of less than 10 mm, the difference is greater than 2 mm and outside the selected range of lordosis. In some embodiments, the threshold value is in a range of 1 through 10 mm corresponding to a selected range of lordosis, as described herein. In some embodiments, one or more components of surgical system 10 provide indicia, a signal, an alert and/or a warning of a H3, H4 difference within and/or without a selected range of threshold value.

In some embodiments, the difference between pre-operative area A1 and intra-operative area A2 is determined and/or calculated, and compared to a threshold value, which corresponds to a selected maximum and/or selected range of lordosis, relative to pre-operative area A1, of an interbody implant 12 to maintain a non-compressed orientation of tissue T of neural foramen F on nerve root N. The threshold value corresponds to a selected lordosis having one or more selected angular orientations of vertebral engaging surfaces of interbody implant 12, similar to that described herein. In one example, area A1 is 23 mm$^2$ and the selected threshold value, which corresponds to a selected maximum and/or selected range of lordosis, relative to pre-operative measurement A1, is 5 mm$^2$. Area A2 is intra-operatively measured and compared to area A1. The difference of A1, A2 is compared to the threshold value. A difference greater than 5 mm$^2$ is outside the selected range of lordosis and a difference of less than 5 mm$^2$ is within the selected range of lordosis. For example, if manipulation of vertebrae V and/or trialing provides an area A2 of less than 18 mm$^2$, the difference is greater than 5 mm$^2$ and outside the selected range of lordosis. In some embodiments, the threshold value is in a range of 1 through 15 mm$^2$ corresponding to a selected range of lordosis, as described herein. In some embodiments, one or more components of surgical system 10 provide indicia, a signal, an alert and/or a warning of a A1, A2 difference within and/or without a selected range of threshold value.

The components of surgical system 10 and the present method include an algorithm and/or formula, similar to those described herein, which utilize parameters, for example, pre-operative and intra-operative measurements H3, H4, and/or A1, A2, to determine and/or calculate a difference of H3, H4 and/or A1, A2, which is compared to a threshold value, which corresponds to a selected maximum and/or selected range of lordosis, relative to the pre-operative measurement, as described herein. In some embodiments, the algorithm and/or formula comprises calculating a numerical difference between H3, H4, and/or A1, A2, and comparing the resulting difference to a selected threshold value.

In some embodiments, the computer of surgical system 10 includes a computer readable medium for storing an algorithm and/or methods that utilize pre-operative and intra-operative measurements H3, H4, and/or A1, A2, to determine and/or calculate a difference that is compared to the threshold value, which corresponds to a selected maximum and/or selected range of lordosis, relative to a pre-operative measurement, as described herein, and may include software programs, applications and codes for determining treatment including selection of the configuration and dimension of interbody implant 12, for example, a selected lordosis of the vertebral engaging surfaces of interbody implant 12. Such software programs, applications and codes being readily prepared by one skilled in the art based on the present disclosure, to be executed by a computer processor of surgical system 10. The processor executes the algorithm to determine the difference that is compared to the threshold value. The computer includes a user interface or monitor that provides indicia, which may include a signal, alert and/or a warning of a difference within and/or without a selected range of threshold value, for example, a numerical representation/display. In some embodiments, the indicia may include human readable visual indicia, human readable tactile indicia and/or audible indicia provided by the computer. In some embodiments, the indicia may include an analog, such as, for example, a dial with a numerical indicator of angle and/or digital display, such as, for example, LED and/or LCD.

In some embodiments, a size of interbody implant 12 is selected based on the difference calculations of H3, H4, and/or A1, A2, and comparison to the threshold value. In some embodiments, interbody implant 12 is visualized by fluoroscopy and oriented before introduction into vertebral space S. Interbody implant 12 is selected based on the threshold value in connection with the present method to achieve segmental lordosis, avoid PI-LL mismatch in an attempt to attain sagittal alignment, and to resist and/or prevent closing of neural foramen F and resulting compression of nerve root N, as described herein. An inserter (not shown) is attached with interbody implant 12 to deliver interbody implant 12 adjacent to a surgical site for implantation adjacent the L4-L5 intervertebral space.

It will be understood that various modifications may be made to the embodiments disclosed herein, Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:
   pre-operatively measuring a first portion of intervertebral tissue adjacent to a neural foramen;
   inserting a trial into an intervertebral disc space of vertebral tissue after pre-operatively measuring the first portion;
   selectively rotating vertebrae of the vertebral tissue relative to one another about the trial;
   intra-operatively measuring a second portion of the intervertebral tissue adjacent to the neural foramen after selectively rotating the vertebrae;
   generating at least one threshold value based on the measured portions; and
   selecting an interbody implant based on the threshold value.

2. A method as recited in claim 1, wherein the threshold value includes a selected angular orientation of vertebral engaging surfaces of the interbody implant.

3. A method as recited in claim 1, wherein the threshold value includes a selected angular orientation of vertebral engaging surfaces of the interbody implant, the selected angular orientation being in a range of 5 through 30 degrees.

4. A method as recited in claim 1, further comprising the step of removing the trial and disposing the interbody implant in the intervertebral disc space, wherein the threshold value includes a selected range of segmental lordosis of the vertebral tissue that resists and/or prevents compression of the neural foramen.

5. A method as recited in claim 1, further comprising the step of removing the trial and disposing the interbody implant in the intervertebral disc space, wherein the threshold value includes a lordosis maximum of the vertebral tissue.

6. A method as recited in claim 1, further comprising the step of measuring the difference of a pelvic incidence and lordosis of vertebral tissue that includes the intervertebral disc space and the step of generating includes the threshold value based on the heights and the difference of the pelvic incidence and the lordosis.

7. A method as recited in claim 1, wherein the portions comprise anatomical proxies.

8. A method as recited in claim 1, wherein the first portion includes a posterior height of an intervertebral disc space.

9. A method as recited in claim 1, wherein the step of pre-operatively measuring includes measuring with medical imaging.

10. A method as recited in claim 9, wherein the medical imaging includes surgical navigation.

11. A method as recited in claim 1, wherein the second portion includes an anterior height of an intervertebral disc space.

12. A method as recited in claim 1, wherein the step of intra-operatively measuring includes measuring with medical imaging.

13. A method for treating a spine, the method comprising the steps of:
pre-operatively measuring at least one dimension of a neural foramen;
inserting a trial into an intervertebral disc space of vertebral tissue after pre-operatively measuring the at least one dimension;
selectively rotating vertebrae of the vertebral tissue relative to one another about the trial;
intra-operatively measuring the at least one dimension after selectively rotating the vertebrae;
comparing the intra-operative measurement of the at least one dimension with a threshold value; and
generating a signal based on the comparison of the measurements and the threshold value.

14. A method as recited in claim 13, further comprising the step of disposing an interbody implant with the intervertebral disc space adjacent the neural foramen and subsequently intra-operatively measuring the at least one dimension.

15. A method as recited in claim 13, wherein the signal includes one or more computer generated indicia.

16. A method as recited in claim 13, wherein the at least one dimension includes a foraminal height.

17. A method as recited in claim 16, wherein the at least one dimension includes an area of the neural foramen.

18. A method as recited in claim 13, wherein the step of pre-operatively measuring includes measuring with medical imaging.

19. A method as recited in claim 13, wherein the step of intra-operatively measuring includes measuring with medical imaging.

* * * * *

UNITED STATES PATENT AND TRADEMARK OFFICE
CERTIFICATE OF CORRECTION

| | | |
|---|---|---|
| PATENT NO. | : 10,172,719 B2 | |
| APPLICATION NO. | : 15/432648 | |
| DATED | : January 8, 2019 | |
| INVENTOR(S) | : Benson et al. | |

It is certified that error appears in the above-identified patent and that said Letters Patent is hereby corrected as shown below:

On the Title Page

In Item (71), under "Applicant", in Column 1, Line 1, delete "Inc," and insert -- Inc., --, therefor.

In the Specification

In Column 4, Line 31, delete "(mm), In" and insert -- (mm). In --, therefor.

In Column 9, Line 37, delete "a of" and insert -- α of --, therefor.

In Column 13, Line 66, delete "Hit" and insert -- $H1^t$ --, therefor.

In Column 14, Line 37, delete "S, Maximum" and insert -- S. Maximum --, therefor.

In Column 15, Line 17, delete "radian," and insert -- radians, --, therefor.

In Column 15, Line 27, delete "$HS^t=H1^2$" and insert -- $HS^t=H1^p$ --, therefor.

In Column 15, Line 32, delete "calcuted" and insert -- calculated --, therefor.

In Column 16, Line 1, delete "32," and insert -- S2, --, therefor.

In Column 16, Line 14, delete "FIG. 19, Area" and insert -- FIG. 19. Area --, therefor.

In Column 16, Line 31, delete "lordosis, Surgical" and insert -- lordosis. Surgical --, therefor.

In Column 18, Line 33, delete "herein, Therefore," and insert -- herein. Therefore, --, therefor.

Signed and Sealed this
Ninth Day of July, 2019

Andrei Iancu
*Director of the United States Patent and Trademark Office*